United States Patent [19]

Kubota

[11] Patent Number: 5,586,226
[45] Date of Patent: Dec. 17, 1996

[54] CONTROL METHOD AND DEVICE FOR A UNICOLOR PRINTER

[75] Inventor: Tsutomu Kubota, Tokyo, Japan

[73] Assignee: Canon Kabushiki Kaisha, Tokyo, Japan

[21] Appl. No.: 429,027

[22] Filed: Apr. 26, 1995

Related U.S. Application Data

[63] Continuation of Ser. No. 92,949, Jul. 19, 1993, abandoned, which is a continuation of Ser. No. 697,598, May 9, 1991, abandoned.

[30] Foreign Application Priority Data

May 16, 1990 [JP] Japan .................................. 2-124246

[51] Int. Cl.$^6$ ...................................................... G06A 15/00
[52] U.S. Cl. ............................................ 395/110; 395/114
[58] Field of Search ...................................... 395/109, 110, 395/114, 115; 358/462, 500, 540; 400/61, 62, 67, 69, 70, 76

[56] References Cited

U.S. PATENT DOCUMENTS

| | | | |
|---|---|---|---|
| 4,516,139 | 5/1985 | Takiguchi | 358/75 |
| 4,587,536 | 5/1986 | Saito et al. | 346/157 |
| 4,651,278 | 3/1987 | Herzog et al. | 395/114 |
| 5,050,098 | 9/1991 | Brown, III et al. | 395/114 |
| 5,051,925 | 9/1991 | Kadono et al. | 395/110 |

*Primary Examiner*—Arthur G. Evans
*Attorney, Agent, or Firm*—Fitzpatrick, Cella, Harper & Scinto

[57] ABSTRACT

A printer control apparatus includes a color-assigned font determining device for determining whether or not a color-assigned font is included in a print font pattern to be downloaded in a connected printer, and a notifying device for notifying a user that a color-assigned font is included in a font pattern downloaded in a printer. If the determination is affirmative, the user is notified of the fact, and can then input processing commands relating to the color-assigned font for output. It is thereby possible to distinguish a font to which a color is assigned from other fonts even when all the fonts are output by a unicolor printer.

38 Claims, 5 Drawing Sheets

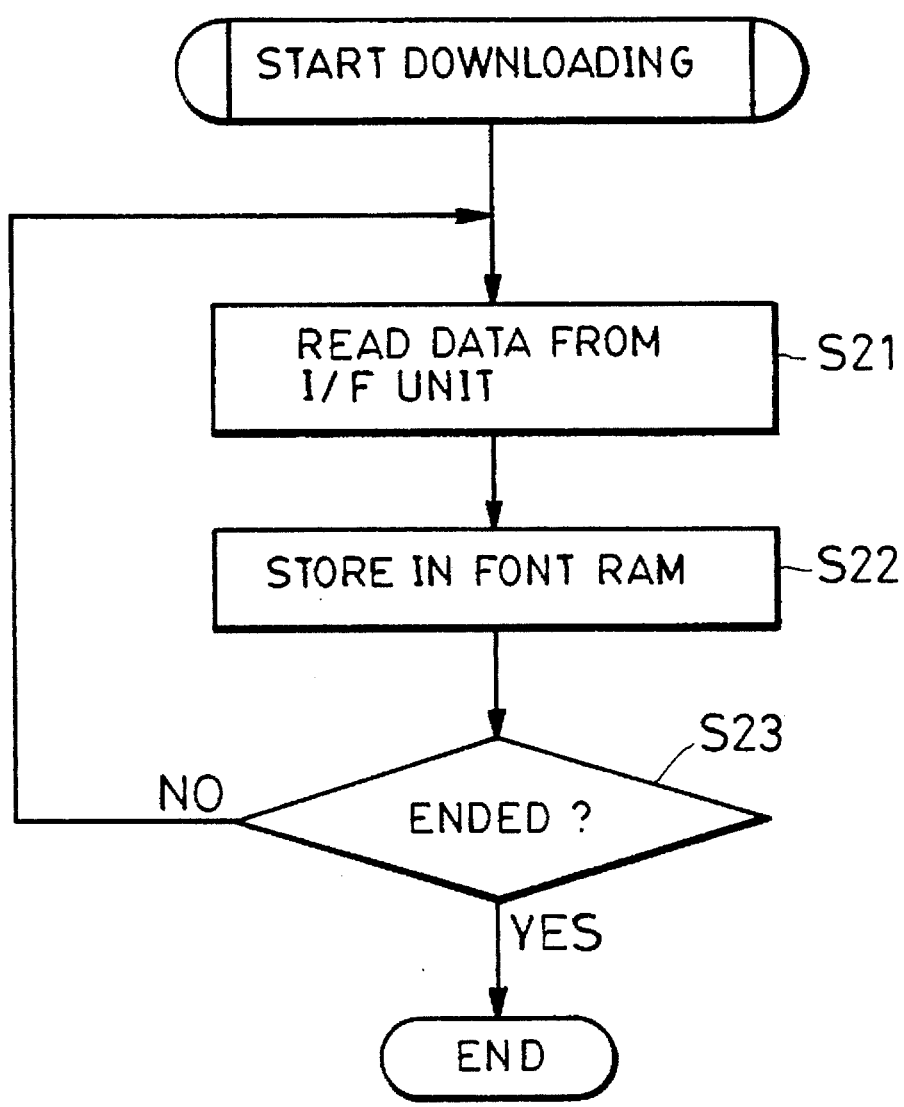

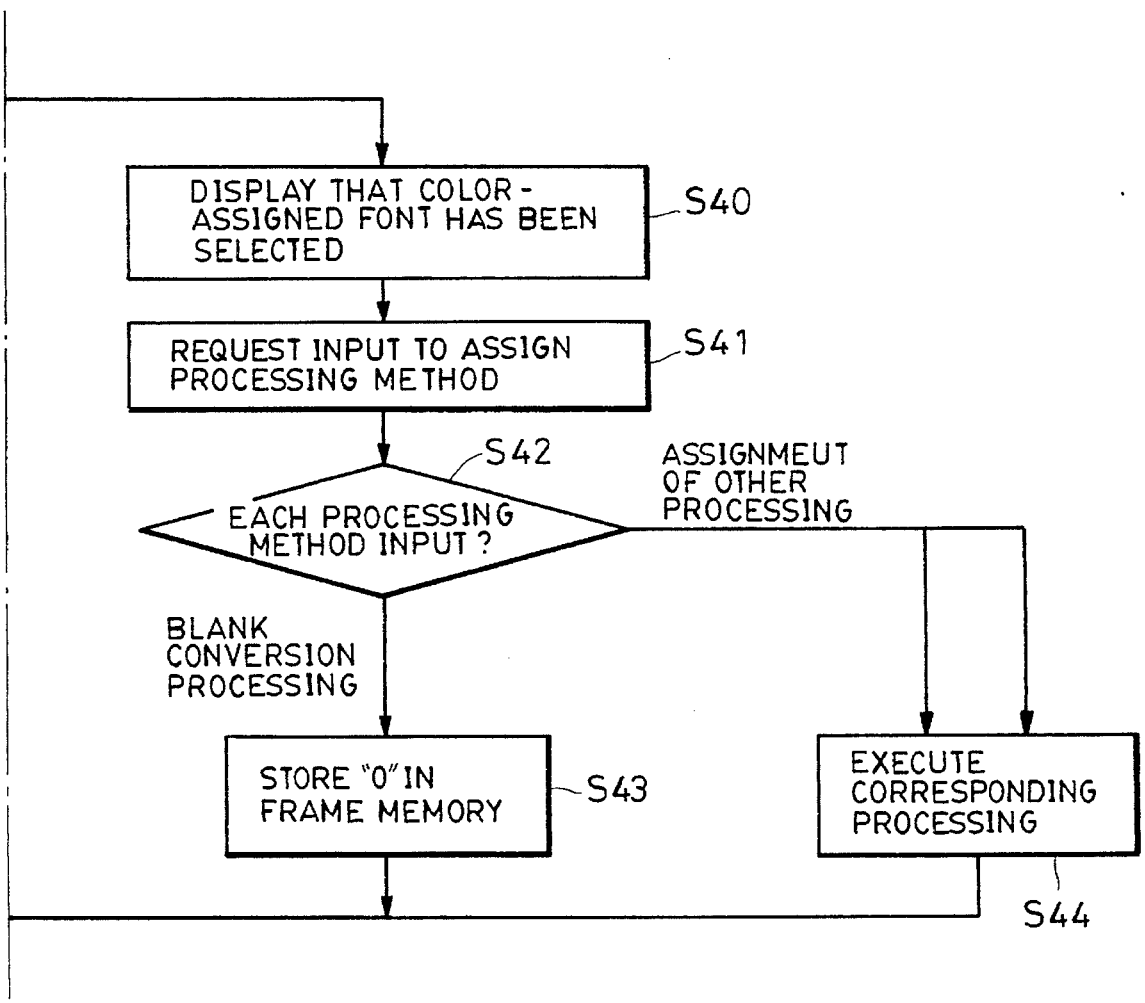

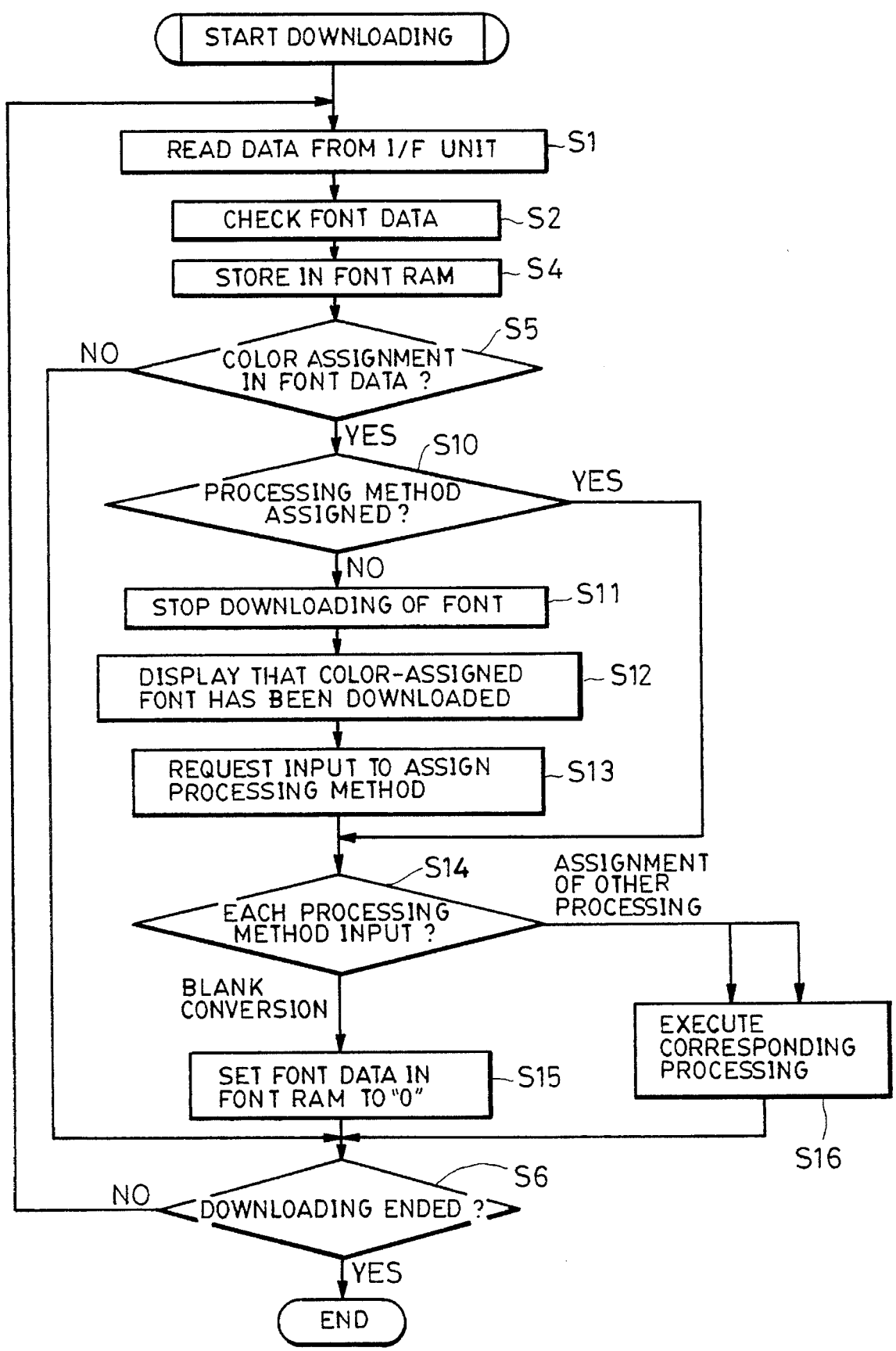

1

CONTROL METHOD AND DEVICE FOR A UNICOLOR PRINTER

This application is a continuation of application Ser. No. 08/092,949, filed Jul. 19, 1993, which in turn is a continuation of application Ser. No. 07/697,598, filed May 9, 1991, both now abandoned.

BACKGROUND OF THE INVENTION

1. Field of the Invention

This invention relates to a printer control method and device wherein a color-assigned font is downloaded on a connected unicolor printer, and the output of the font can be controlled.

2. Description of the Related Art

Heretofore, even if a color-assigned font is downloaded on a unicolor printer, and printing is performed assigning the font, the color assigned for the font has not been reproduced in printing, and printing has been performed in the same color as when using other fonts to which a color is not assigned.

Accordingly, the prior art has the disadvantage that the object of distinguishing the color-assigned font from other fonts cannot be achieved.

SUMMARY OF THE INVENTION

According to the present invention, it is possible to provide a printer control method and device which detects that a font downloaded on a printer is a color-assigned font, and notifies the user of the fact. It becomes thereby possible to perform the expansion of data in a bit image, and the like, according to a processing program or method assigned by the user for the data using the font, and to print the color-assigned font so as to distinguish the font from other fonts even with a unicolor printer.

According to a first aspect of the present invention, print font pattern data of a print font is downloaded into a control apparatus for a printer. The control apparatus includes a font receiving device for receiving the print font pattern data downloaded from the print font. Control circuitry is coupled to the font receiving device and determines whether the downloaded print font pattern data includes color font data.

According to another aspect of the present invention, a method of controlling a printer includes the steps of receiving downloaded print font pattern data from a print font and determining whether color font data is included in the downloaded print font pattern data.

According to yet a further aspect of the present invention, a control apparatus includes an input data receiving device for receiving input data including color and/or non-color input data and a font storage memory for storing print font pattern data including color font data. Control circuitry is coupled to the input data receiving device and the font storage memory and determines whether color input data is included in the received input data.

According to still a further aspect of the present invention, a method of controlling a printer includes the steps of receiving input data including color and/or non-color input data, storing print font pattern data including color font data and determining whether color input data is included in the received input data.

BRIEF DESCRIPTION OF THE DRAWINGS

FIG. 2 is a flowchart showing downloading processing in the first embodiment;

FIG. 4 is a flowchart showing downloading processing of a second embodiment of the present invention.

DETAILED DESCRIPTION OF THE PREFERRED EMBODIMENTS

An explanation will now be provided of preferred embodiments of the present invention with reference to the drawings.

Figure 1:
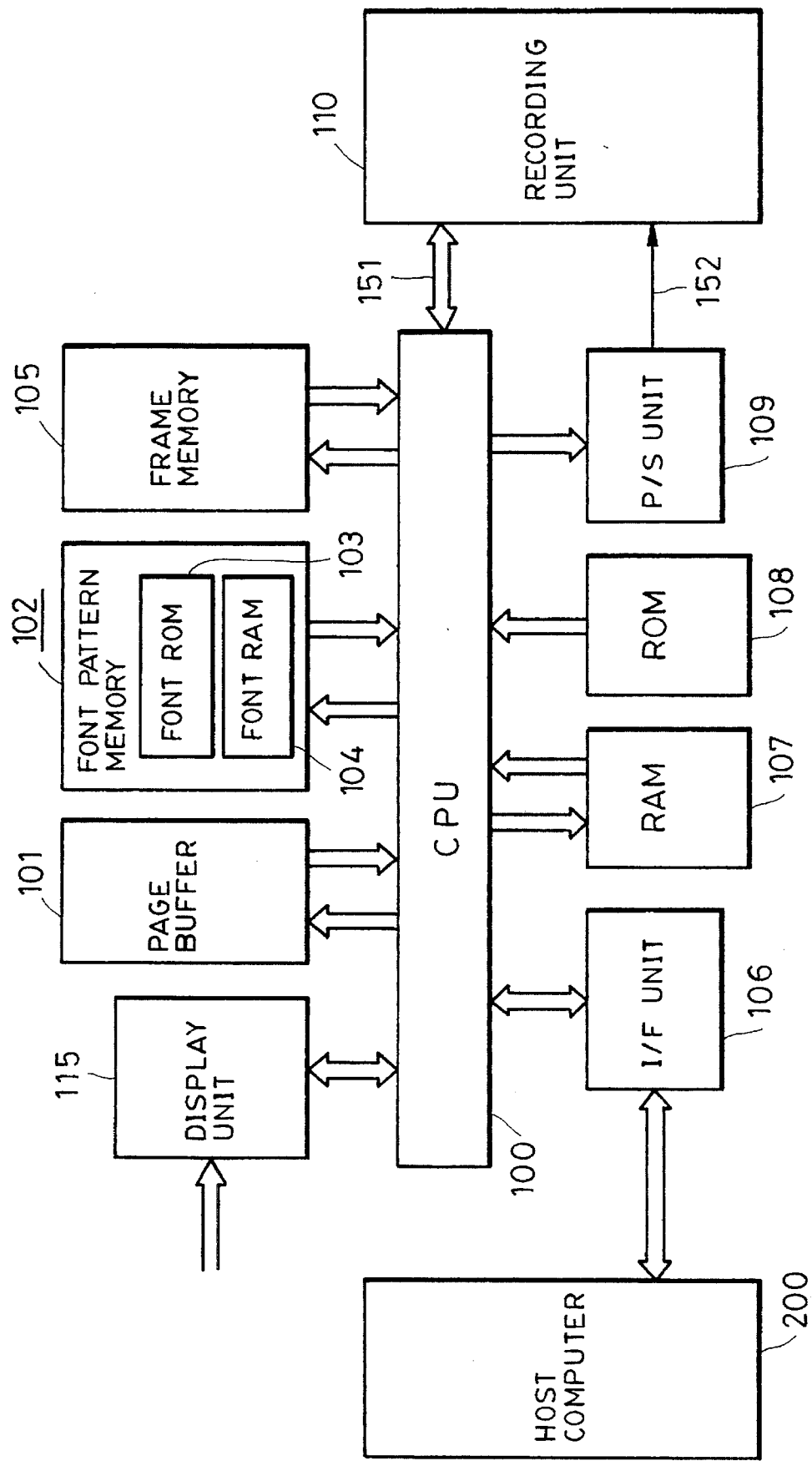
FIG. 1 is a block diagram of the configuration of a system according to a first embodiment of the present invention.

FIG. 1 is a block diagram of the configuration of a system according to a first embodiment of the present invention.

In FIG. 1, a CPU (central processing unit) 100 controls the entire system, for example, in accordance with programs for controlling processing shown in FIGS. 2 and 3 (to be described later) stored within a ROM (read-only memory) 108. A page buffer 101 temporarily stores data transmitted from a host computer (hereinafter termed a "host") 200. A font pattern memory 102 stores character patterns corresponding to character codes, and includes a font ROM 103 and a font RAM (random access memory) 104 for storing fonts to be downloaded from the host 200 and the like. A frame memory 105 stores bit image data, serving as output patterns for a recording unit 110. An interface (I/F) unit 106 performs communication with the host 200. There is also shown a RAM 107 for work. A parallel-serial (P/S) conversion unit 109 converts parallel recording data from the CPU 100 into serial video signal data, and outputs the converted data. The recording unit 110 prints the video signal data from the P/S unit 109 on a recording medium as corresponding image data. Control signal line 151 performs transmission/reception of control signals with the recording unit 110. Video signal line 152 transmits video signals, serving as data, to the recording unit 110. The host 200 outputs recording data and the like.

Figure 3A:
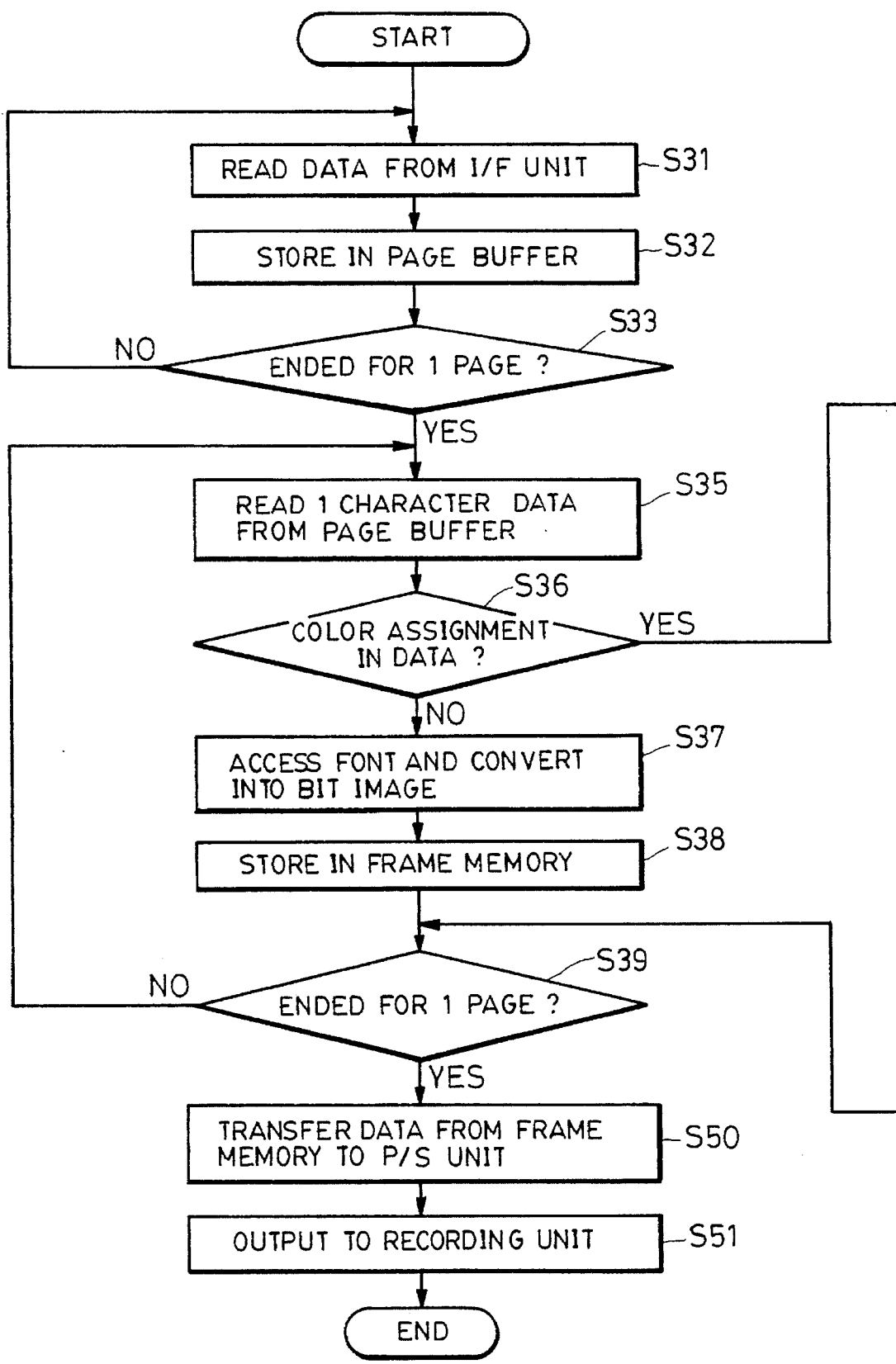
FIG. 3, composed of FIGS. 3A and 3B, is a flowchart showing printing processing of the first embodiment.

An explanation will now be provided of the processing operation of the present embodiment having the configuration shown in FIG. 1 with reference to flowcharts shown in FIGS. 2 and 3.

First, an explanation will be provided of downloading processing of a font pattern of the embodiment with reference to the flowchart shown in FIG. 2.

When a request for downloading a font has been transmitted from the host 200 to the I/F unit 106, a downloading operation is started, and the control by the CPU 100 proceeds to downloading processing shown in FIG. 2.

First, at step S21, the CPU 100 reads the font pattern downloaded from the host 200 via the I/F unit 106. At step S22, the downloaded font pattern is written in the font RAM 104. At step S23, it is checked whether or not all the downloading operations have been completed and all the received data have been stored. If it has been determined that fonts to be downloaded are still present, the process returns to step S21, where the next downloaded font is stored.

When all the downloading operations have been completed, and all the received data have been stored in the font RAM 104, the downloading processing is terminated.

Next, an explanation will be provided of printing processing of the present embodiment with reference to the flowchart shown in FIG. 3.

When printing data have been transmitted from the host 200, the control by the CPU 100 proceeds to printing processing shown in the flowchart of FIG. 3. First, at step S31, the CPU 100 reads printing data from the host 200 via the I/F unit 106. At step S32, the read printing data are transferred to and stored in the page buffer 101. At step S33, it is checked whether or not printing data for one page have been read and stored. If the reception of printing data for one page has not been completed, the process returns to step S31, where the next printing data are received and stored.

When printing data for one page have been stored in the page buffer 101 repeating steps S31–S33, the process proceeds from step S33 to step S35, where the CPU 100 reads data for one character from among the printing data (code data) stored in the page buffer 101, and checks whether or not color assignment is present in the read data at step S36. If color assignment is absent, the process proceeds to step S37, where the data are converted into bit image data corresponding to the printing data using font data stored in the font ROM 103 or the font RAM 104. At step S38, the bit image data are stored in the frame memory 105. At step S39, it is checked whether or not the printing data for one page have been converted into the corresponding bit image data and expanded in the memory 105. If the result of the check is negative, the process returns to step S35, where the next printing data are converted and expanded.

If the bit image data for one page have been stored and expanded in the frame memory 105, the process proceeds from step S39 to step S50, where the CPU 100 outputs the data to the parallel-serial (P/S) conversion unit 109. At step S51, the data are converted into the corresponding video signals by the P/S conversion unit 109, and the converted signals are transmitted to the recording unit 110. Characters represented by the signals are printed on a recording medium by the recording unit 110.

If color assignment is present in the read printing data as a result of the check at step S36, and a font corresponding to the printing data is present, the process proceeds to step S40, where expansion of the data are temporarily stopped, and the display unit 115 displays that data for printing the color-assigned font are present. At step S41, an input for assigning a processing method for the data is requested. At step S42, a command input for the precessing method corresponding to the request is awaited, and processing in accordance with the command input is performed. For example, if there has been a command input indicating that printing of color-assigned characters and the like is not to be performed, the process proceeds from step S42 to step S43, where the CPU 100 writes data "0" (a blank image wherein nothing is printed) in the frame memory 105. The process then proceeds to step S39. In the present case, code data are sequentially expanded in the frame memory 105. If any data for printing the color-assigned font are still present, data for printing nothing are written in the frame memory 105.

Command processing is not limited to the above-described blank conversion processing. If there has been any other command input, the process proceeds from step S42 to step S44, where the processing corresponding to the command input is executed, and the corresponding image data are stored in the frame memory 105. The process then proceeds to step S39. At step S44, for example, processing to convert the image data into inverted image data and to store the inverted data in the frame memory 105 is performed. There is of course a case wherein no conversion processing is performed and the data are converted into the same pattern as when color assignment is absent.

Code data are sequentially expanded in the frame memory 105. If any data for printing the color-assigned font are still present, data for printing nothing are written in the frame memory 105. When bit image data for one page have been stored in the frame memory 105, the CPU 100 transmits the data to the parallel-serial (P/S)conversion unit 109, which converts the transmitted data into video signals, and transmits the converted signals to the recording unit 110 to perform printing.

Heretofore, a unicolor printer has been incapable of dealing with patterns for which a particular font must be used because they are not easily distinguished or their images are in some cases distorted absent color, such as the national flag of Japan, the logotype of a corporation, and the like. In the present embodiment, however, the pattern is not necessarily printed with the same color (black or the like) as other portions, and it is also possible to select processing dealing with such a problem.

In the foregoing embodiment, it is determined whether or not color assignment is included within printing data, the subsequent processing is changed in accordance with the result of the determination, and any other font arriving during a downloading operation of a font pattern is stored in the font memory 102 without modification. However, the present invention is not limited to the above-described example. It may be determined whether or not a color-assigned font is present during the downloading operation of a font pattern, and processing corresponding to the result of the determination may be performed.

An explanation will now be provided of a second embodiment of the present invention wherein the above-described processing is performed.

Hardware in the second embodiment may have the same configuration as in the first embodiment shown in FIG. 1.

An explanation will now be provided of downloading processing of the second embodiment with reference to a flowchart shown in FIG. 4.

When a request for downloading a font has been transmitted from the host 200 to the I/F unit 106, a downloading operation is started, and the control of the CPU 100 proceeds to downloading processing shown in FIG. 4

First, at step S1, the CPU 100 reads a font pattern first downloaded from the host 200 via the I/F unit 106. At step S2, data of the downloaded font (color-assigned data in the present embodiment) are checked. At step S4, the downloaded font pattern is written in the font RAM 104. At step S5, it is checked whether or not color assignment is included within the font. If the result of check is negative, the process proceeds to step S6, where it is checked whether or not all the downloading operations have ended, and all the received data have been stored. If any fonts to be downloaded are still present, the process returns to step S1, where the next downloaded font is stored.

When all the downloading operations have ended, and all the received data have been stored, the processing is terminated.

On the other hand, if color assignment has been included in the font data at step S5, the process proceeds to step S10. At step S10, if a command for which processing is to be performed when a font including color assignment is downloaded has not previously been input, the process proceeds to step S11, where the downloading operation of a font is temporarily stopped. At step S12, the display unit 115 displays that a color-assigned font has been downloaded. At step S13, an input for assigning a processing method for the data is requested. At step S14, a command input for the processing method corresponding to the request is awaited, and processing in accordance with the command input is performed. For example, if there has been a command input indicating that a blank image, wherein nothing is printed, is to be output when a color-assigned font is assigned, the process proceeds from step S14 to step S15, where the CPU 100 writes data "0" (representing a blank image wherein nothing is printed) in the corresponding font position of the RAM 104. The process then proceeds to step S6.

The command processing at step S14 is not limited to the above-described blank conversion processing. If there has been any other command input, the process proceeds from step S14 to step S16, where the processing corresponding to the command input is executed, and the corresponding converted font data are stored in the font RAM 104. The process then proceeds to step S6. At step S16, for example, processing to convert the image data into inverted image data and to store the inverted data in the font RAM 104 is performed. There is of course a case wherein no conversion processing is performed, and the data remain in the same pattern as when color assignment is absent.

In the present embodiment, the succeeding operation to expand the data in bit images and print the data is entirely the same as in a usual case. That is, in the processing shown in FIG. 3, the determination processing at step S36 is not performed, and the process may directly proceed from step S35 to step S37.

As explained above, according to the present embodiment, even when a color-assigned font is downloaded on and used in a unicolor printer, it is possible to prevent in advance printing of patterns which become meaningless in a different color (such as the national flag of Japan and the like), or whose image is damaged (such as the logotype of a corporation and the like), by notifying the fact that the color-assigned font is downloaded.

What is claimed is:

1. A control apparatus for a printer, said control apparatus comprising:

font receiving means for receiving font pattern data;

determining means for determining whether the font pattern data include color data; and notifying means for notifying that the font pattern data include color data when said determining means determines that the font pattern data include color data, wherein said notifying means further provides an output signal when the font pattern data include color font data and requests, through the output signal, that an input processing program be assigned to the color font data, said input processing program being input from an external host apparatus.

2. A control apparatus according to claim 1, wherein said determining means determines whether the font pattern data include color font data as the font pattern data is being received by said receiving means.

3. A control apparatus according to claim 1, further including means for receiving color and non-color input data, wherein control circuitry converts the non-color input data into output data in accordance with the font data and converts the color input data into output data in accordance with the requested processing program.

4. A control apparatus according to claim 1, further comprising means for displaying, in response to the output signal from said notifying means, both an indication that the downloaded print font pattern data include color font data and a request for a processing program.

5. A control apparatus according to claim 3, wherein said control circuitry converts the color input data into blank output data in accordance with said input processing program input from said external host apparatus.

6. A control apparatus according to claim 3, wherein said control circuitry converts the color input data into inverted output data in accordance with said input processing program input from said external host apparatus.

7. A control method for controlling a printer, said method comprising the steps of:

receiving font pattern data;

determining whether color data are included in the font pattern data; and notifying that the font pattern data include color data when it is determined in said determining step that the font pattern data include color data, wherein in said notifying step an output signal is provided when the font pattern data include color data and it is requested, through the output signal, that an input processing program be assigned to the color font data, said input processing program being input from an external host apparatus.

8. A printer control method according to claim 7, wherein said determining step is performed concurrently with said receiving step.

9. A printer control method according to claim 7, further comprising the steps of receiving color and non-color input data and converting the non-color input data into output data in accordance with print font pattern data and converting the color input data into output data in accordance with the requested processing program.

10. A printer control method according to claim 7, further comprising the step of displaying, in response to the output signal, both an indication that the downloaded font pattern data include color font data and a request for a processing program.

11. A printer control method according to claim 9, wherein the color input data are converted into blank output data in said converting step in accordance with said input processing program input from said external host apparatus.

12. A printer control method according to claim 9, wherein the color input data are converted into inverted output data in said converting step in accordance with said input processing program input from said external host apparatus.

13. A control apparatus for a printer, said apparatus comprising:

means for receiving input data including at least one of color and non-color input data;

font storage means for storing print font pattern data including color font data; and control circuitry, coupled to said receiving means and said font storage means, for determining whether color input data are included in the received input data and for notifying that the font pattern data include color data when said control circuitry determines that the font pattern data include color data, wherein said control circuitry further provides an output signal when the received input data include color data and requests, through the output signal, that an input processing program be assigned to the color data, said input processing program being input from an external host apparatus.

14. A control apparatus according to claim 13, wherein said control circuitry further converts the non-color input data into output data in accordance with the print font pattern data and converts the color input data into output data in accordance with the requested processing program, the output data to be printed by the printer.

15. A control apparatus according to claim 13, further comprising means for displaying, in response to the output signal from said control circuitry, both an indication that the received input data include color input data and a request for a processing program.

16. A control apparatus according to claim 14, wherein said control circuitry converts the color input data into blank output data in accordance with said input processing program input from said external host apparatus.

17. A control apparatus according to claim 14, wherein said control circuitry converts the color input data into inverted output data in accordance with said input processing program input from said external host apparatus.

18. A control method for controlling a printer, said method comprising the steps of:

receiving input data including at least one of color and non-color input data;

storing print font pattern data including color font data;

determining whether color input data are included in the received input data; and notifying that the font pattern data include color input data when it is determined in said determining step that the font pattern data include color input data, wherein in said notifying step an output signal is provided when the received input data include color input data and it is requested, through the output signal, that an input processing program be assigned to the color input data, said input processing program being input from an external host apparatus.

19. A printer control method according to claim 18, further comprising the steps of converting the non-color input data into output data in accordance with the print font pattern data and converting the color input data into output data in accordance with the requested processing program, the output data to be printed by the printer.

20. A printer control method according to claim 18, further comprising the step of displaying in response to the output signal, both an indication that the received input data include color input data and a request for a processing program.

21. A printer control method according to claim 19, wherein the color input data are converted into blank output data in accordance with said input processing program input from said external host apparatus.

22. A printer control method according to claim 19, wherein the color input data are converted into inverted output data in accordance with said input processing program input from said external host apparatus.

23. An apparatus according to claim 1, further comprising means for determining whether an output method is assigned in the font pattern data.

24. An apparatus according to claim 7, further comprising the step of determining whether an output method is assigned in the font pattern data.

25. A control apparatus for printing, said apparatus comprising:

means for reading code data for one character;

means for determining whether color assignment is present in the read code data; and means for notifying that the code data include color assignment when the presence of color assignment is determined by said determining means, wherein said notifying means further provides an output signal when the code data include color assignment and requests, through the output signal, that an input processing program be assigned to the color assignment, said input processing program being input from an external host apparatus.

26. An apparatus according to claim 25, further comprising means for inputting an output method of a color-assigned character.

27. An apparatus according to claim 25, wherein the output method comprises forming a blank image, said blank image being formed in accordance with said input processing program input from said external host apparatus.

28. An apparatus according to claim 25, wherein the output method comprises forming an inverted image, said inverted image being formed in accordance with said input processing program input from said external host apparatus.

29. An apparatus according to claim 25, wherein the output method comprises forming non-color-assigned characters and color-assigned characters distinguishably.

30. An apparatus according to claim 26, wherein the output method comprises forming a blank image, said blank image being formed in accordance with said input processing program input from said external host apparatus.

31. An apparatus according to claim 26, wherein the output method comprises forming an inverted image, said inverted image being formed in accordance with said input processing program input from said external host apparatus.

32. An apparatus according to claim 26, wherein the output method comprises forming non-color-assigned characters and color-assigned characters distinguishably.

33. An apparatus according to claim 25, wherein the notification by said notifying means is displayed.

34. A control apparatus according to claim 1, further comprising said printer.

35. A control method according to claim 7, wherein said output signal is provided to said printer.

36. A control apparatus according to claim 13, further comprising said printer.

37. A control method according to claim 18, wherein said output signal is provided to said printer.

38. A control apparatus according to claim 25, further comprising said printer.

\* \* \* \* \*

UNITED STATES PATENT AND TRADEMARK OFFICE
CERTIFICATE OF CORRECTION

PATENT NO. : 5,586,226
DATED : December 17, 1996
INVENTOR(S) : Kubota

It is certified that error appears in the above-indentified patent and that said Letters Patent is hereby corrected as shown below:

In the Drawing:

SHEET 4 OF THE DRAWINGS:

In FIG. 3B, "ASSIGNMEUT" should read --ASSIGNMENT--.

COLUMN 5:

Line 45, "data" should read --data,--.

COLUMN 6:

Line 55, "data" (second occurrence) should read --data,--.

COLUMN 7:

Line 51, "An apparatus" should read --A method--.

COLUMN 8:

Line 10, "assignment" should read --assignment,--.

Signed and Sealed this

Seventeenth Day of June, 1997

BRUCE LEHMAN

Attest:

Attesting Officer

Commissioner of Patents and Trademarks